(12) United States Patent
Polley et al.

(10) Patent No.: US 6,837,873 B1
(45) Date of Patent: Jan. 4, 2005

(54) METHOD AND AN APPARATUS FOR FORMING A ONE-PIECE INTRODUCER

(75) Inventors: William F. Polley, San Marcos, CA (US); Fidelis C. Onwumere, Loveland, OH (US)

(73) Assignee: Medex, Inc., Carlsbad, CA (US)

( * ) Notice: Subject to any disclaimer, the term of this patent is extended or adjusted under 35 U.S.C. 154(b) by 0 days.

(21) Appl. No.: 09/753,355

(22) Filed: Dec. 29, 2000

(51) Int. Cl.[7] .......................................... A61M 5/178
(52) U.S. Cl. ................. 604/164.01; 604/160; 604/171; 604/177
(58) Field of Search ................................ 604/158–177

(56) References Cited

U.S. PATENT DOCUMENTS

| | | | | |
|---|---|---|---|---|
| 4,411,654 A | * | 10/1983 | Boarini et al. | 604/165.04 |
| 4,581,025 A | * | 4/1986 | Timmermans | 604/264 |
| 4,596,559 A | * | 6/1986 | Fleischhacker | 604/164.05 |
| 4,772,266 A | * | 9/1988 | Groshong | 604/164.05 |
| 4,983,168 A | | 1/1991 | Moorehead | |
| 5,167,634 A | * | 12/1992 | Corrigan et al. | 604/160 |
| 5,188,605 A | * | 2/1993 | Sleep | 604/158 |
| 5,190,528 A | * | 3/1993 | Fonger et al. | 604/171 |
| 5,250,033 A | * | 10/1993 | Evans et al. | 604/160 |
| 5,263,938 A | * | 11/1993 | Orr et al. | 604/171 |
| 5,334,157 A | * | 8/1994 | Klein et al. | 604/160 |
| 5,409,463 A | * | 4/1995 | Thomas et al. | 604/167.04 |
| 5,489,273 A | * | 2/1996 | Whitney et al. | 604/160 |
| 5,782,817 A | * | 7/1998 | Franzel et al. | 604/256 |
| 6,027,480 A | * | 2/2000 | Davis et al. | 604/164.05 |
| 6,183,443 B1 | * | 2/2001 | Kratoska et al. | 604/164.03 |
| 6,336,914 B1 | * | 1/2002 | Gillespie, III | 604/165.01 |

* cited by examiner

*Primary Examiner*—Henry Bennett
*Assistant Examiner*—Amanda Flynn
(74) *Attorney, Agent, or Firm*—Wood, Herron & Evans, LLP

(57) ABSTRACT

A method and an apparatus for forming a one-piece introducer in which at least one finger tab is formed at one end of a tube. The apparatus is formed from a molton polymer fed into the cavity of a mold. The cavity of the mold has a portion that forms a tube and a portion that forms a tab.

11 Claims, 11 Drawing Sheets

METHOD AND AN APPARATUS FOR FORMING A ONE-PIECE INTRODUCER

BACKGROUND OF THE INVENTION

Field of the Invention

This invention relates generally to intravascular assemblies, and more specifically to the body of a one-piece introducer and method of making the one-piece introducer.

BACKGROUND

Intravascular devices such as catheter assemblies are generally used for passing fluids between a device such as a syringe or a drip to or from body lumens such as veins or arteries, or other internal target sites. Such an assembly usually includes a hub, and a catheter tube. The tube is typically secured to the hub by means of an eyelet ring that is press fit within the nose of the hub. This hub and tube assembly is then mounted over an introducer needle comprising a sharp needle attached to a plastic hub. The sharp tip of the needle, protruding from the catheter tip, is used for piercing a body lumen so that access may be gained into the body lumen by the needle and subsequently the catheter. Once the catheter and the needle are located within the body lumen, the introducer needle is removed and discarded while the catheter tube remains in the body lumen. A syringe or a tube of a drip is then attached to the hub so that fluids may be passed through the hub and the catheter from the drip or the syringe to the body lumen. The hub is typically made of materials that provide sufficient rigidity thereto and the catheter tube is usually made of a material which is flexible.

If a catheter is to be repeatedly inserted into a patient, an introducer may be used with the catheter to reduce the number of times a patient's skin must be punctured in order to gain access to a body lumen such as a vein. Introducers serve to guide the insertion of a catheter into a blood vessel.

A typical catheter introducer may be considered as having a relatively short tubular sheath, open at its distal end (the end within the patient), and a housing attached to the proximal end (outside of the patient) of the sheath. The housing typically includes a proximal aperture through which a catheter can be passed as well as a self-sealing valve or gasket to effect a seal to prevent blood from leaking out of the introducer, both when a catheter is passed through the introducer as well as when the catheter has been withdrawn from the introducer. The housing also may include a side port through which blood may be sampled or medication or other physiological liquids may be introduced. Such catheter introducers are in common use in angiography, angioplasty, or other procedures.

The catheter and catheter introducer are used in the following manner. The hollow needle is first advanced through the skin, the subcutaneous tissue and into the body lumen (e.g., blood vessel) of interest. A guidewire then is advanced through the hollow needle and into the blood vessel. While maintaining that position of the guidewire, the needle then is withdrawn proximally and is separated from the guidewire. With the sheath mounted on a dilator which is coupled to the needle for dilating a blood vessel, the dilator then is threaded onto the proximal end of the guidewire and is advanced along the guidewire toward and into engagement with the puncture site. The distal tapered end of the dilator facilitates insertion of the tip of the dilator into the puncture by progressively dilating the puncture as the dilator is advanced through the tissue. Such progressive dilation of the puncture site is intended to facilitate advancement of the still larger diameter introducer sheath into and through the puncture site so that together they can be advanced along the guidewire into the blood vessel. When the distal portion of the sheath has been advanced into the blood vessel, the dilator and guidewire can be removed, leaving the catheter introducer in place and in readiness to receive and direct other guidewires, catheters or other appropriate instruments into and from the blood vessel.

A conventional introducer 10, illustrated in FIG. 1, generally includes three components such as a tube (or dilator) 20, a self-sealing valve 50, and molded finger tabs 40. As illustrated in FIGS. 1 and 2, a scoreline 30 may be added along tube 20 to make it easier for a healthcare worker to break apart tube 20 when removing the introducer while leaving the catheter, needle or instrument 60 in the patient. Conventional introducers are costly because tube 20, self-sealing valve 50, and molded finger tabs 40 must be manufactured separately and then assembled. It is therefore desirable to have a method of fabricating a one-piece introducer that is able to reduce the operational costs associated with conventional devices such as the cost of assembling the tube and hub.

SUMMARY

A method is disclosed in which a polymer in a molten state is fed into a cavity of a mold. The polymer may be fed into the mold using a variety of methods such as conventional injection molding, multi-injection molding, co-injection of one or more polymers at or about the same time into the mold, gas assist molding or other suitable method. A first portion of the cavity has at least one finger tab. The second portion of the cavity is a tube. After the molten polymer has filled the cavity of the mold, the polymer is cooled and a one-piece introducer is then formed. In another embodiment, the introducer lumen is formed by either gas-assist or a core pin inserted into the mold. The technique that is used may depend upon the overall length and size of introducer.

In another embodiment, a one-piece introducer for an intravascular device is disclosed. The one-piece introducer includes at least one finger tab portion, a tube portion, and a hinge portion between the finger tab portion and the tube portion. Additional features, embodiments, and benefits will be evident in view of the figures and detailed description presented herein.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention in which.

DETAILED DESCRIPTION

One embodiment of the invention relates to forming a one-piece introducer by injection molding of polymer(s) into a mold using a variety of techniques such as injection molding, multi-injection molding, co-injection molding, and gas assist molding. The mold can have a variety of shapes. In one embodiment, a first portion of the cavity of the mold has at least one finger tab. The second portion of the cavity is a tube. After the molten polymer has filled the cavity of the mold, the polymer is cooled and a one-piece introducer is then formed.

Referring to the figures, exemplary embodiments of the invention will now be described. The exemplary embodiments are provided to illustrate aspects of the invention and should not be construed as limiting the scope of the invention.

Presented below is a description of the materials that may be used followed by a process description of forming a one-piece introducer. Next, several embodiments are presented of the various molds that may be used to form a variety of one-piece introducers.

The materials that may be used for injection molding of the one-piece introducer include liquid crystal polymers such as that which is commercially available as VECTRA™ from TICONA™, a division of Hoechst (Summit, N.J.) and XYDAR™ commercially available from Amoco Polymers, Inc. located at Alpharetta, Ga. Additionally, other polymers may be used such as polyetheramides, polycarbonate, polyester with glass fiber, polyester with carbon filler, polyamide with glass fiber, thermoplastic elastomers, e.g., CFLEX™, commercially available from Consolidated Polymer Technology located in Largo, Fla.; KRATON™ commercially available from GLS Corporation, Thermoplastic Elastomers Division located in McHenry, Ill.; polyurethane, and SANTOPRENE™ commercially available from Advanced Elastomer Systems located in Akron, Ohio; polyolefins and polyamide with carbon filler. Liquid crystal polymer is the preferred material to be used in this process.

Figure 1:
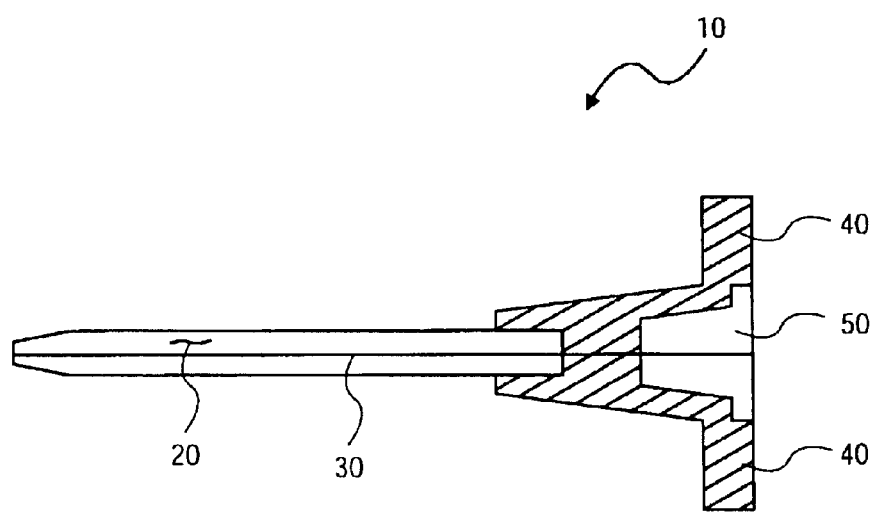
FIG. 1 illustrates a schematic cross-sectional view of an introducer in which a tube, a self-sealing valve, and finger molded tabs are assembled according to the prior art.
Figure 2:
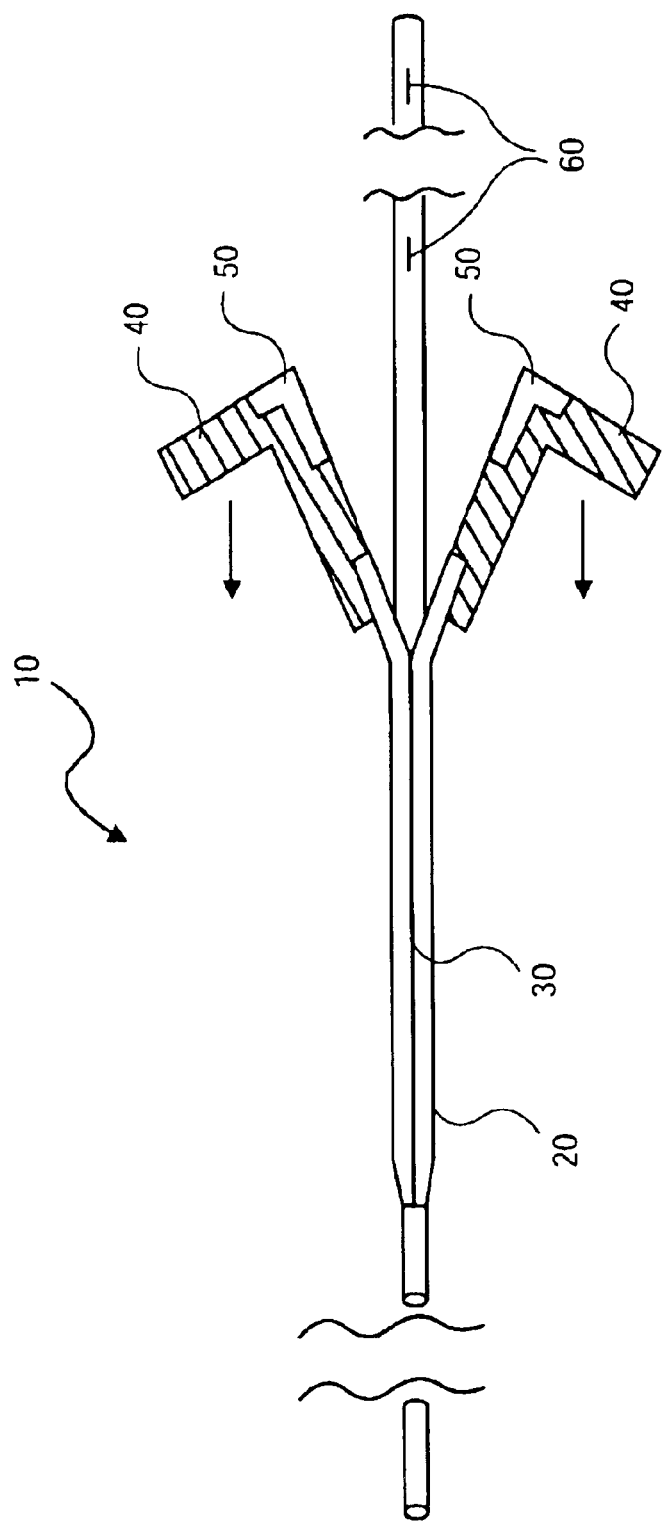
FIG. 2 illustrates a schematic cross-sectional view of an introducer in which a scoreline, added to the tube, is used to peel apart the introducer of the prior art.
Figure 3:
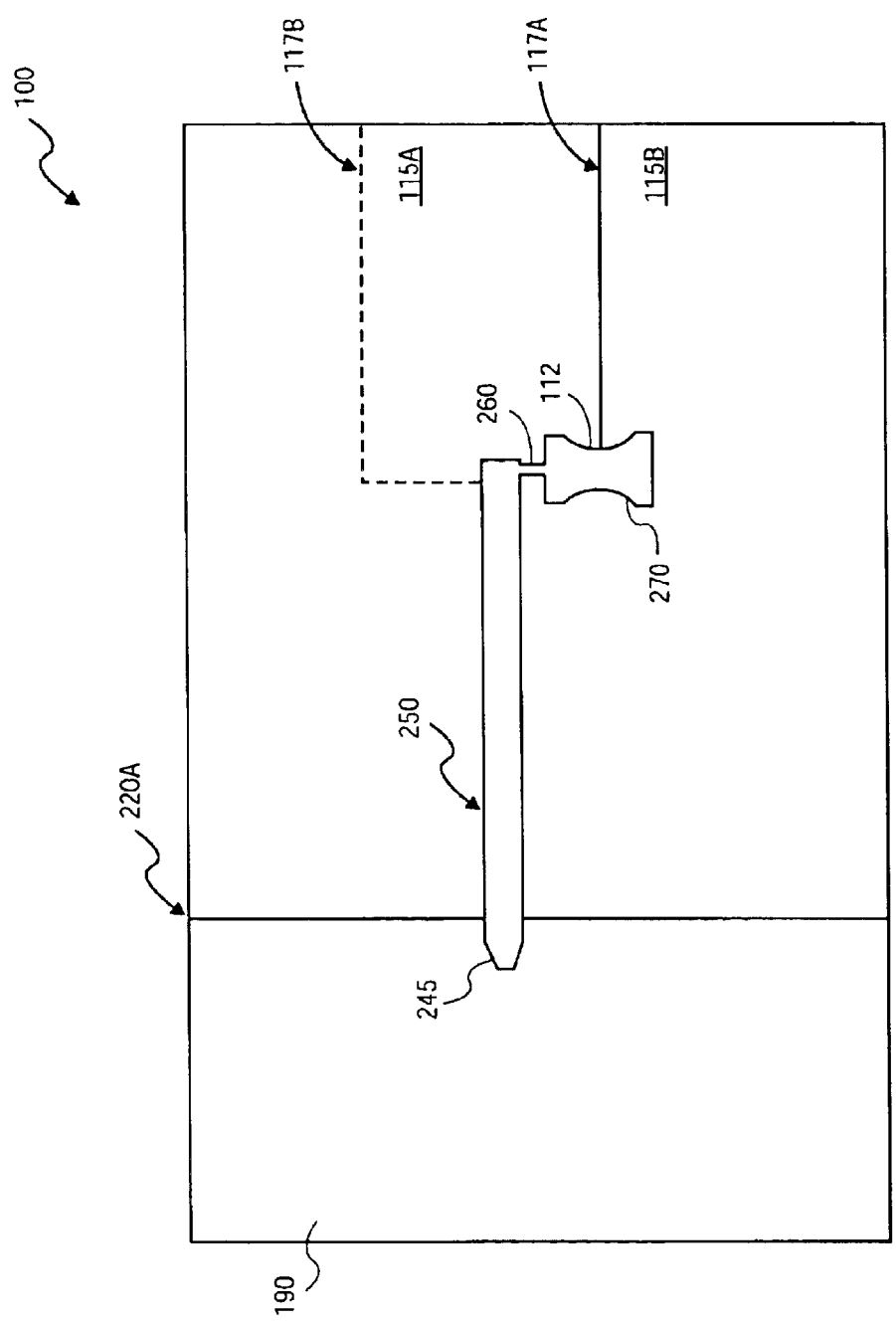
FIG. 3 illustrates a schematic cross-sectional view of a mold comprising three sections which are mated together and the polymer(s) are shown entering the cavity in accordance with one embodiment of the invention.

FIG. 3 illustrates one embodiment of the invention for introducing molten polymer into mold 100. The molten polymer is introduced into mold 100 using a variety of known methods such as injection molding, multi-injection molding, co-injection molding, gas assist molding or other suitable method. FIG. 3 illustrates mold 100 including first and second sections 115a and 115b and third section 190 that are mated together. The cavity formed by mold 100 includes tube portion 250 having a beveled distal tip 245, a finger tab portion 270, and a hinge 260 between tube portion 250 and finger tab portion 270, and a safety valve 247. Hinge 260 and tube portion 250 that are formed from this process are hollow. Hinge 260 may also be solid. In one embodiment, the tab portion 220 of the cavity may define a rectangular, cylindrical, spherical or square shaped tab.

The cavity formed by mold 100 includes an insert (not shown) in order to create space in tube portion 250 and hinge 260. Inserts, known in the art, are disposed in tube portion 250 and hinge 260 of mold 100 such that molten polymer moves around and surrounds the insert. The insert is removed from the one-piece introducer using conventional methods after the polymer has cooled, forming a hollow portion in tube portion 250 and hinge 260.

Mold 100 has an inlet 112 that allows molten polymer to enter mold 100. Alternatively, if two polymers are to be injected into mold 100, inlets 117a and 117b may be used for each polymer. The molten polymer is introduced at inlet 112 of mold 100 at a pressure in the approximate range of 1,000 psi to 5,000 psi and a temperature that ranges from 200° C. to 340° C. It will be appreciated that other pressures and temperatures may be used depending upon the material selected.

The dimensions of the cavity that is formed from sections 115a, 115b, and 190 varies with the gauge of the intravascular assembly to be fabricated. In this embodiment, the one-piece introducer that is formed has a hollow tube with a hollow tip. The outer diameter of the tube cavity may range from about 0.70 millimeters (mm) to about 5.0 mm. The inner diameter of the tube cavity may range from about 0.50 mm to 4.7 mm.

Given the description of mold 100, the path of the molten polymer that is introduced to mold 100 is described below. The molten polymer enters inlet 112 and fills finger tab portion 270. The molten polymer then enters hinge 260 and travels into tube portion 250 and surrounds the insert (not shown) in tube portion 250. The polymer stops at the distal end of tube portion 250. It will be appreciated that the molds described herein may have a runner (not shown) located, for example, at the distal end of tube portion 250 that allows excess polymer to exit the cavity.

Once the polymer cools, the mold opens at parting line 220a. After the mold is opened, the one-piece introducer is then removed or ejected from mold 100 using conventional techniques.

Figure 4:
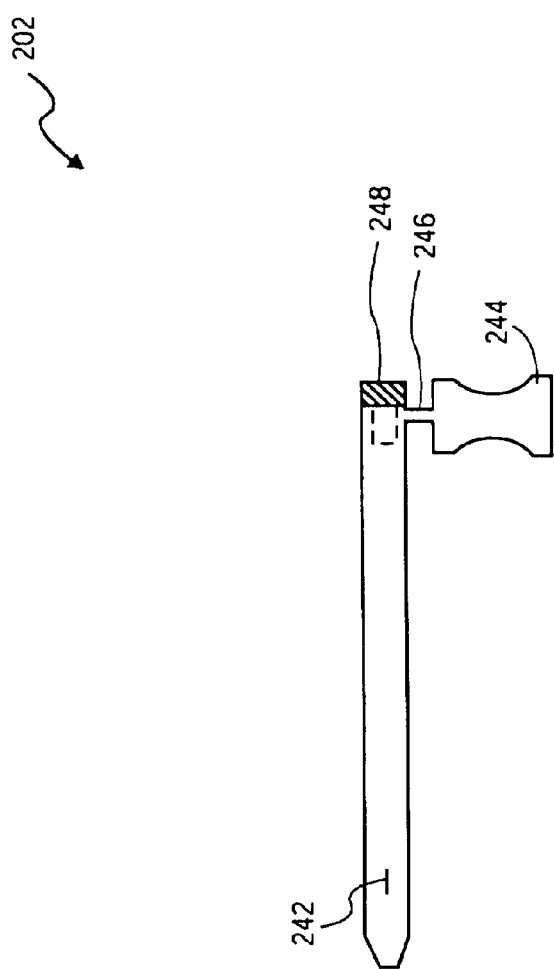
FIG. 4 illustrates a schematic cross-sectional view of a one-piece introducer formed from the mold illustrated in FIG. 3 in accordance with one embodiment of the invention.
Figure 5:
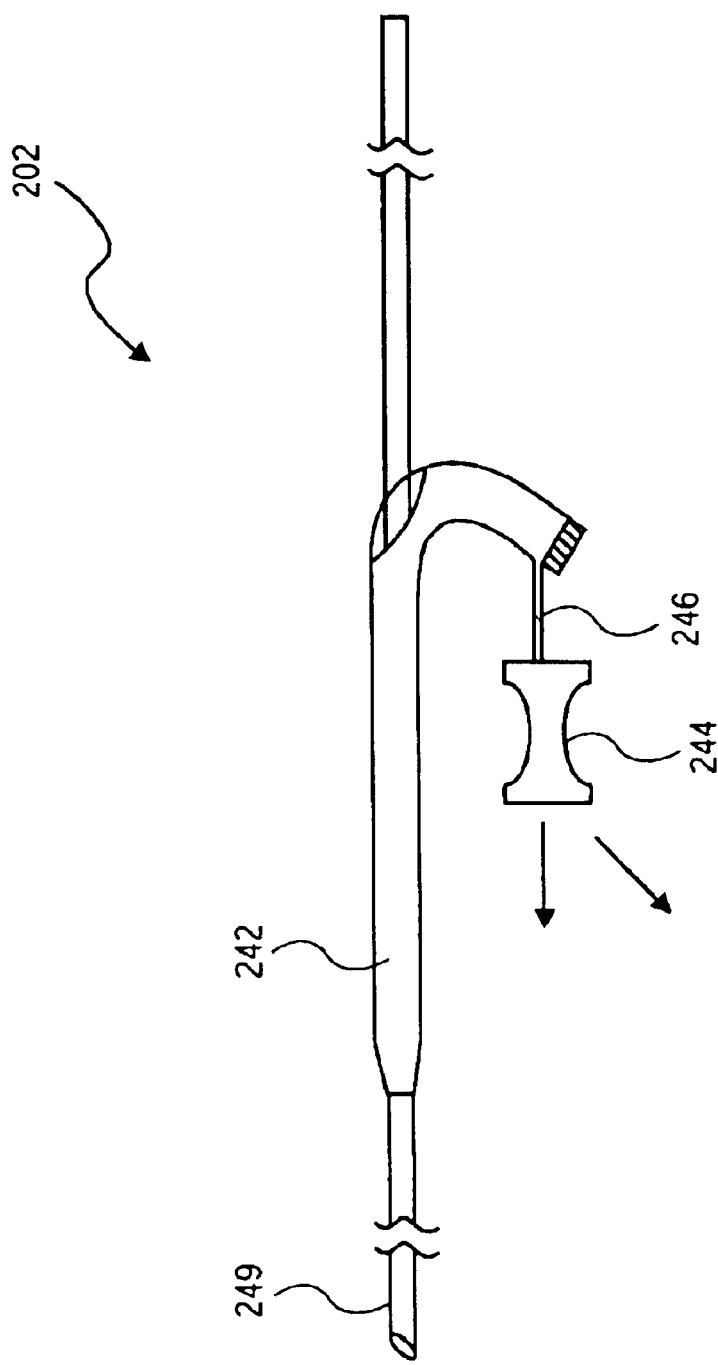
FIG. 5 illustrates a schematic cross-sectional view of one-piece introducer in which the finger tab is used to peel away the tube in accordance with one embodiment of the invention.

FIGS. 4 and 5 illustrate one-piece introducer 202 formed from mold 100 illustrated in FIG. 3 in accordance with one embodiment of the invention. As shown in FIG. 4, tube 242, living hinge 246, and finger tab 244 are formed as a single entity. Safety valve 248 is subsequently secured to one-piece introducer 202 or may be formed during the molding process. FIG. 5 illustrates finger tab 244 used to peel away tube 242 from instrument or catheter 249 in accordance with one embodiment of the invention. Finger tab(s) are pulled to remove the introducer from the catheter or instrument 249 at the distal end of catheter or instrument 249. It will be appreciated that a scoreline, which is used to make it easier to pull away finger tab 244 from catheter 249, may or may not be formed from the process described herein. Preferably, however, the scoreline is formed during the filing of the cavity for mold 100. FIGS. 6–11 illustrate various other embodiments of the invention using, for example, gas assist in order to form a variety of one-piece introducers.

Figure 6:
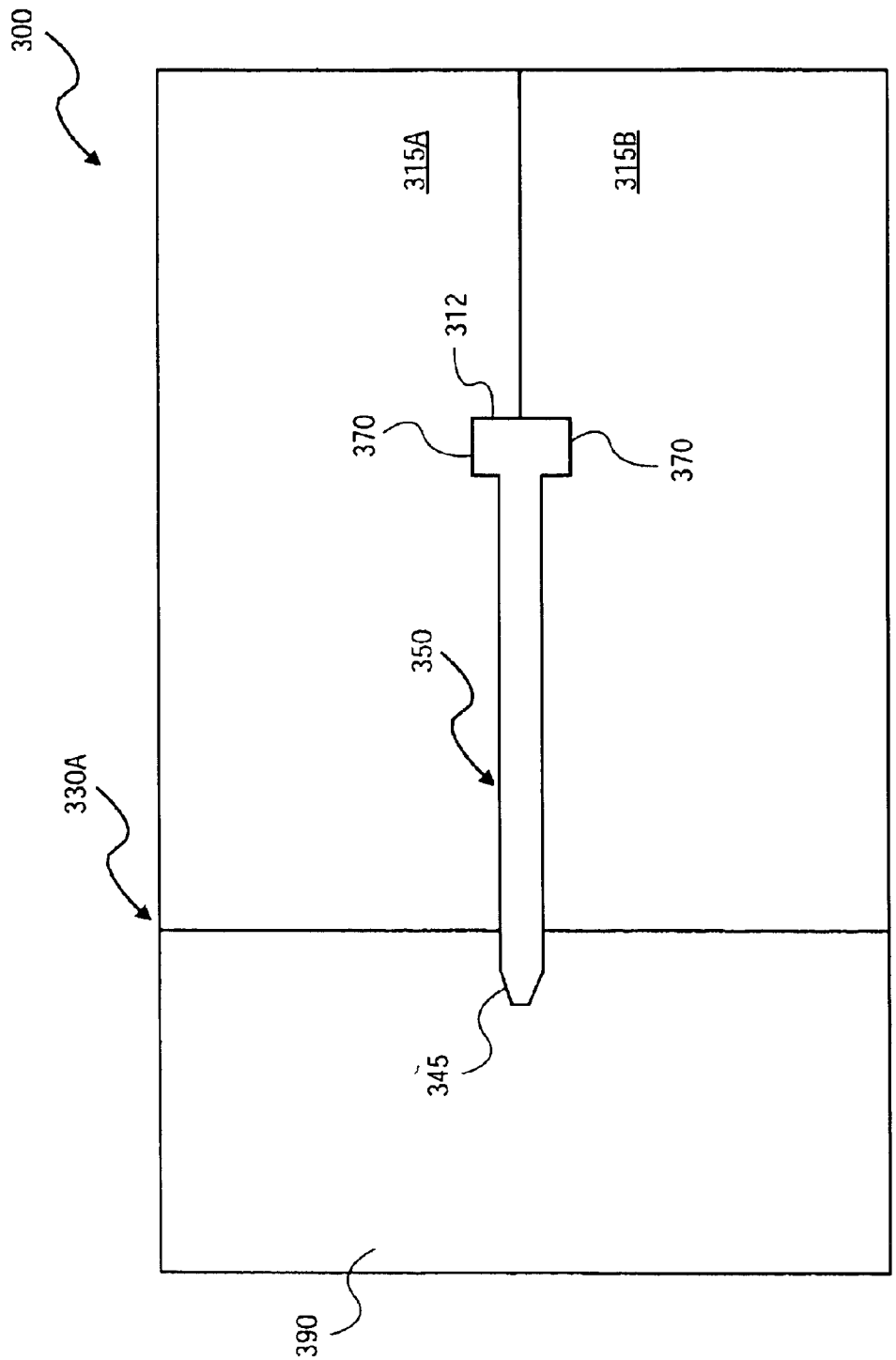
FIG. 6 illustrates a schematic cross-sectional view of a mold to form a one-piece introducer in accordance with one embodiment of the invention.

FIG. 6 illustrates one embodiment of the invention using injection molding to form another type of one-piece introducer. Specifically, FIG. 6 illustrates mold 300 that includes first and second sections 315a, and 315b, and third section 390 mated together at parting line 330a. The cavity formed by mold 300 includes tube portion 350 and two finger tab portions 370 that appear to form a head-shape for the one-piece introducer. Mold 300 further includes a beveled distal tip 345 at the distal end of tube portion 350. Mold 300 has an inlet 312 that allows molten polymer to enter mold 300. The cavity formed by mold 300 includes an insert (not shown) in order to create a hollow space in tube portion 350. Inserts, known in the art, are disposed in tube portion 350 in mold 300 such that molten polymer moves around and surrounds the insert. The insert is removed from the one-piece introducer using conventional methods after the polymer has cooled, forming a hollow portion in tube portion 350. The molten polymer is introduced at inlet 312 of mold 300 at a pressure about in the range of 1,000 psi to 5,000 psi and at a temperature that ranges from about 200° C. to 340° C. It will be appreciated that other pressures and temperatures may be used depending upon the material selected.

It will be appreciated that the dimension of the one-piece introducer that is formed from sections 315a, 315b, and 390 of mold 100 may vary with the gauge of the intravascular assembly to be fabricated. For example, the overall length of the one-piece introducer that is formed may range in length from about 13 mm to about 230 mm. The thickness of tube portion, derived by subtracting the inner diameter from the outer diameter divided by two, may range from about 0.1 mm to about 3.5 mm.

Given the description of mold 300, the path of the molten polymer is presented below. The molten polymer enters inlet 312 and fills finger tab portions 370. The polymer then enters tube portion 350 and surrounds the insert (not shown) in tube portion 350. The polymer stops at the distal end of tube portion 350.

Figure 7:
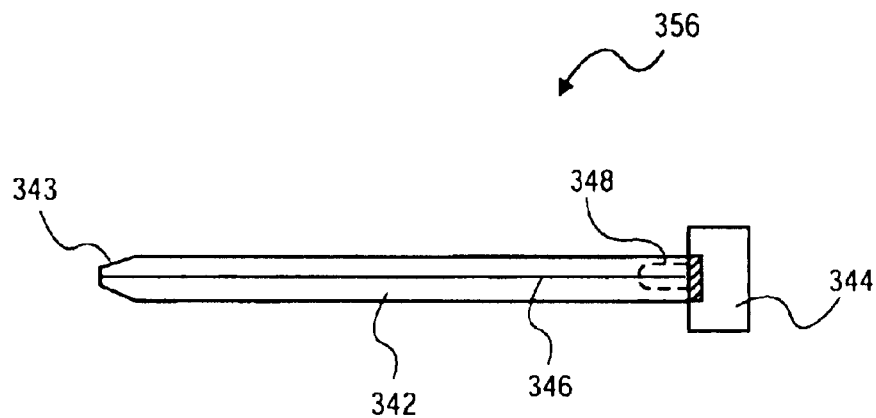
FIG. 7 illustrates a schematic cross-sectional view of the one-piece introducer formed from the mold illustrated in FIG. 6 in accordance with one embodiment of the invention.
Figure 8:
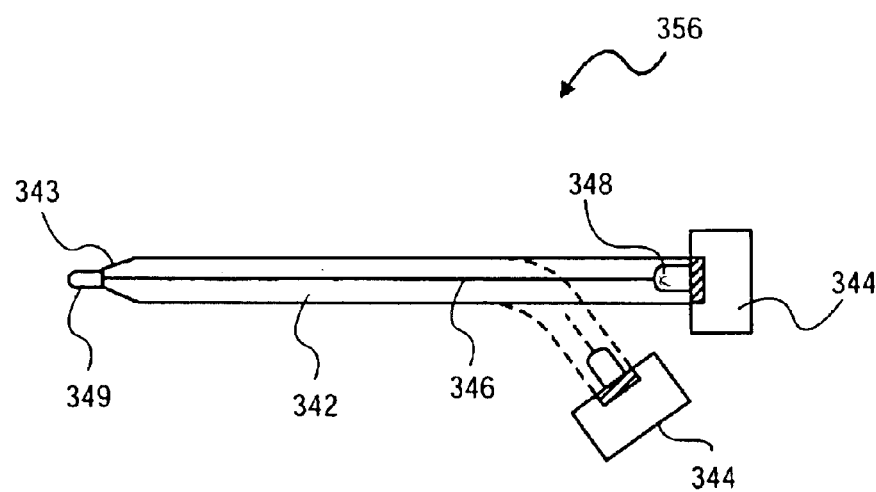
FIG. 8 illustrates a schematic cross-sectional view of a finger tab used to peel away the tube in accordance with one embodiment of the invention.

FIGS. 7 and 8 illustrate one-piece introducer 356, formed from mold 300 of FIG. 6, has tube 342 that has a double distal tip 343 formed with finger tab 344. Safety valve 348 is thereafter inserted into and secured to one-piece introducer 356. Alternatively, safety valve 348 may be formed during the molding process by configuring mold 300 to include a cavity portion for safety valve 348. It will be appreciated that scoreline 346 may or may not be formed from the process and may be added subsequent to the process. Preferably, however, scoreline 346 is formed during the filing of the cavity for mold 300. One-piece introducer 356, formed from mold 300, is shown in FIG. 8 to have finger tab 344 move in a downward direction peeling tube 342 along scoreline 346 away from needle 349.

Figure 9:
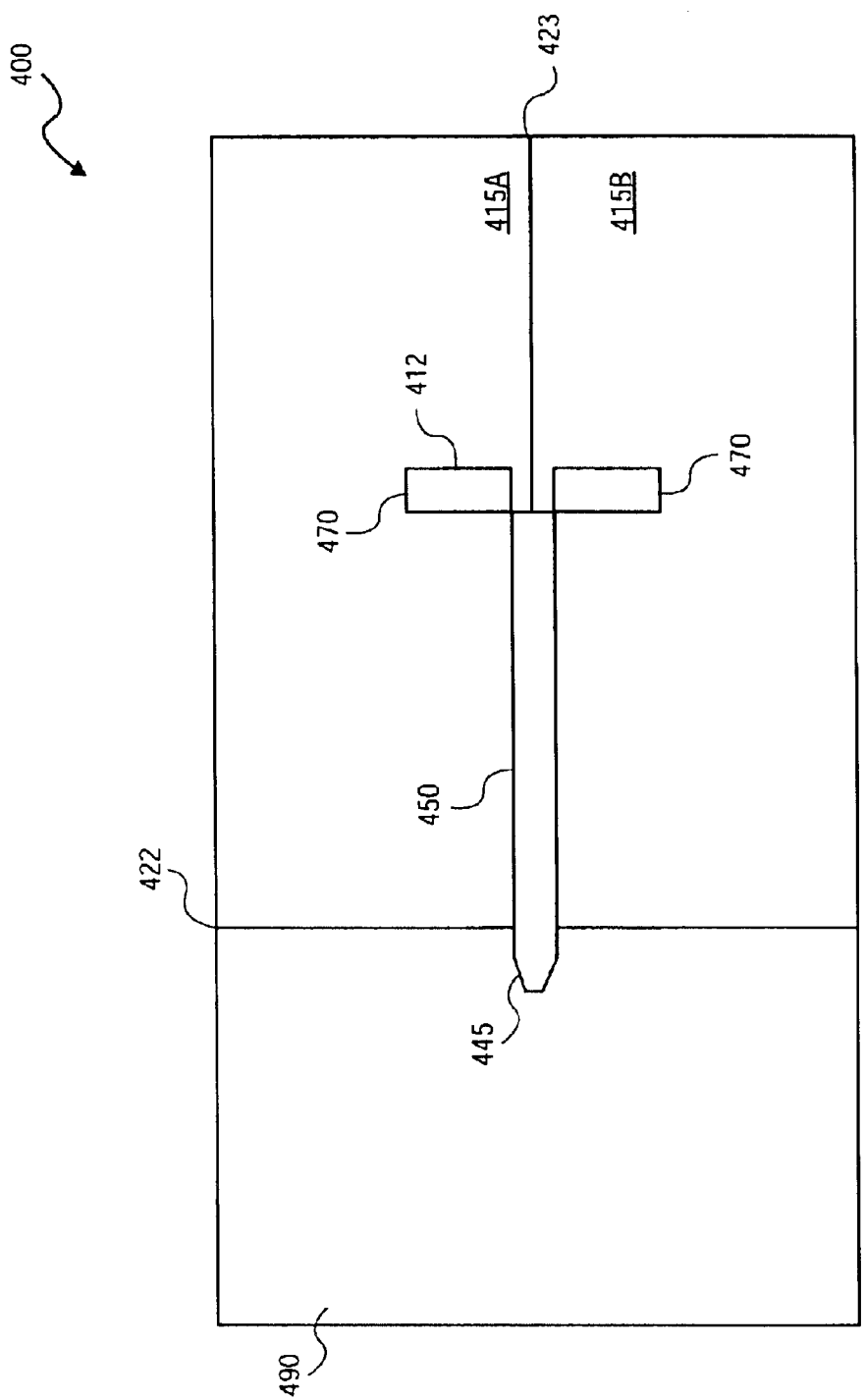
FIG. 9 illustrates a schematic cross-sectional view of a mold to form a one-piece introducer in accordance with one embodiment of the invention.

FIG. 9 illustrates one embodiment of the invention using injection molding to form another type of one-piece introducer. FIG. 9 specifically illustrates mold 400 that includes first and second sections 415a, 415b, and third section 490 mated together. The cavity formed by mold 400 further includes a tube portion 450 and two finger tab portions 470. Mold 400 further includes a beveled distal tip 445 at the distal end of the tube portion 450.

Mold 400 has an inlet 412 that allows molten polymer to enter mold 400. The molten polymer is introduced at inlet 412 of mold 400 at a pressure about in the range of 1,000 psi to 5,000 psi and at a temperature that ranges from about 200° C. to 340° C. It will be appreciated that other pressures and temperatures may be used depending upon the material selected.

It will be appreciated that the dimension of the one-piece introducer that is formed from sections 415a, 415b, and 490 of mold 400 may vary with the gauge of the intravascular assembly to be fabricated. For example, the overall length of the one-piece introducer formed from mold 400 may range in length from about 13 mm to about 230 mm.

The molten polymer enters inlet 412 and fills finger tabs 470 and travels through tube portion 450 around an insert (not shown) in tube portion 450. The mold opens at parting lines 422 and 423 after the polymer has cooled. After the mold is opened, the one-piece introducer is then removed from mold 400 using conventional techniques.

Figure 10:
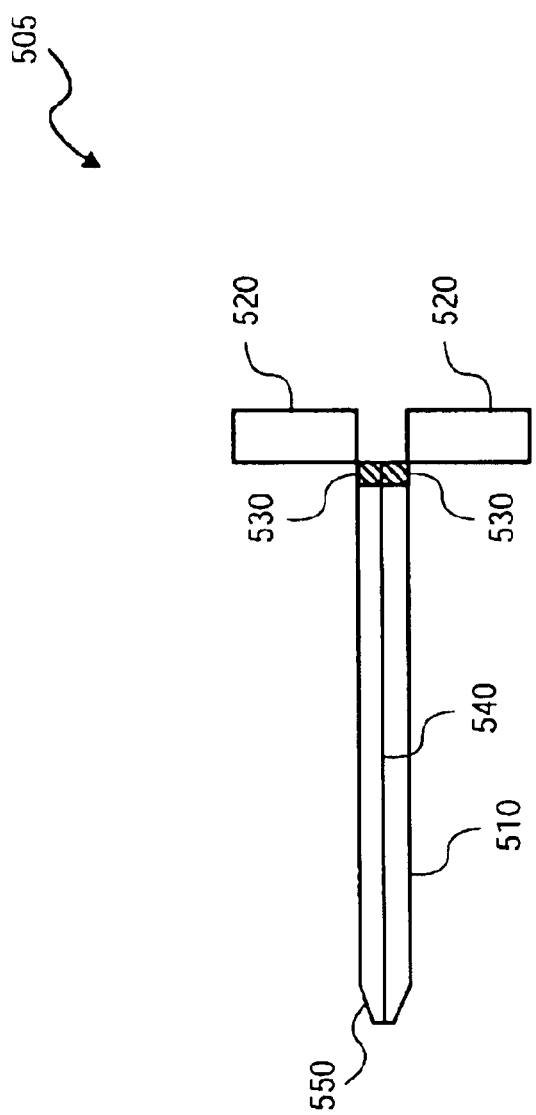
FIG. 10 illustrates a schematic cross-sectional view of a one-piece introducer formed in accordance with one embodiment of the invention.
Figure 11:
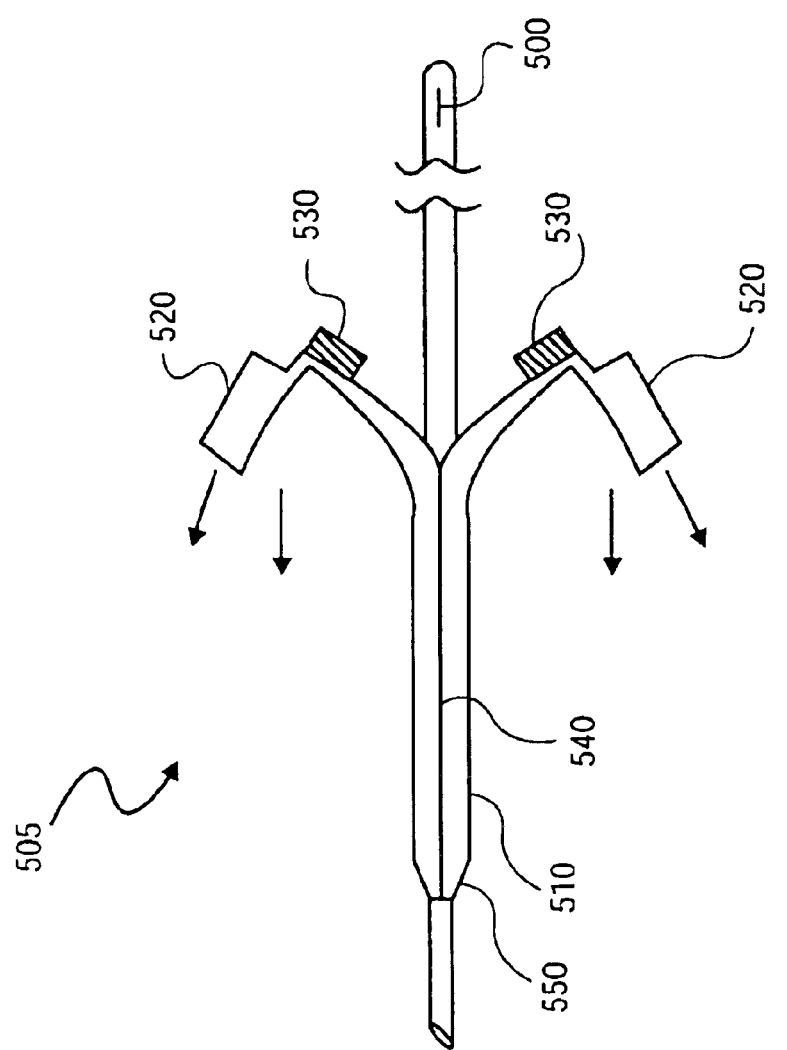
FIG. 11 illustrates a schematic cross-sectional view of the one-piece introducer in which the finger tabs used to pull away the tube at a scoreline in accordance with one embodiment of the invention.

FIGS. 10 and 11 illustrate one-piece introducer 505 formed from mold 400 illustrated in FIG. 9. Introducer 505 has opposing finger tabs 520 and tube 510 that has a beveled distal tip 550. Scoreline 540 formed along tube 510 allows tube 510 to be peeled away after a healthcare worker has inserted a catheter or needle (not shown) into a patient. It will be appreciated that one-piece introducer 505 may be formed without a scoreline. Valve 530 is a self-sealing valve that is inserted into tube 510 or the self-sealing valve is formed in the molding process.

FIG. 11 illustrates a catheter or instrument 500 inserted through introducer 505. Finger tabs 520 are pulled away from catheter or instrument 500. Valves 530 are separated from catheter or needle 500 allowing tube 510 to be peeled away from catheter or instrument 500. After one-piece introducer 505 has been used, one-piece introducer 505 is discarded in accordance with local environmental regulations.

Figure 12:
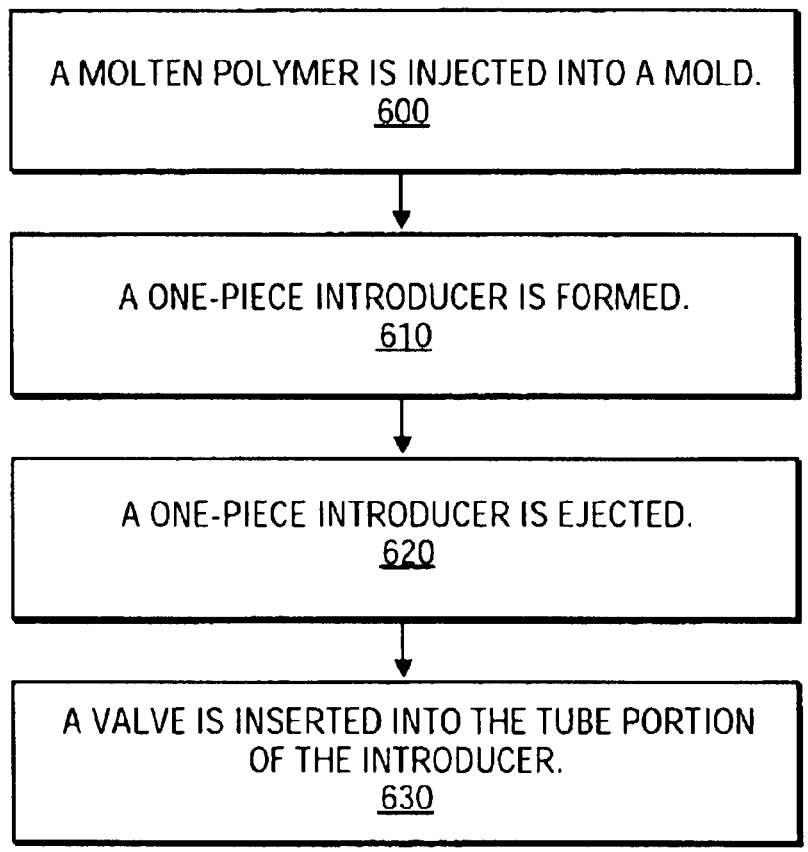
FIG. 12 illustrates a flow diagram of one method for forming a one-piece introducer in accordance with one embodiment of the invention.

FIG. 12 illustrates a flow diagram of one method in accordance with one embodiment of the invention. At block 600, a polymer in a molten state is introduced into a mold. The mold includes a cavity partitioned into a tube portion having a beveled distal tip, at least one finger tab portion, and a hinge between the tube portion and the finger tab portion. It is appreciated that tube portion of the cavity includes an insert or other suitable device in order to ensure that the tube that is formed is hollow. At block 610, a one-piece introducer is formed. At block 620, a one-piece introducer is ejected from the mold. At block 630, a valve such as a self-sealing valve is inserted into the tube portion of the introducer.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A one-piece introducer comprising:
    at least one finger tab portion;
    a tube portion having a scoreline; and
    a valve formed at a proximal end of the tube portion, wherein the at least one finger tab portion, the tube portion, and the valve are formed as a single integral piece.

2. The one-piece introducer of claim 1, comprising a polymer selected from the group consisting of liquid crystal polymer, polyetheramide, polycarbonate, polyester with glass fiber, polyester with carbon filler, polyamide with glass fiber, thermoplastic elastomers, polyolefins and polyamide with carbon filler.

3. The one-piece introducer of claim 1, wherein the tube portion is substantially hollow.

4. The one-piece introducer of claim 1, wherein the finger tab portion has a shape which is one of substantially rectangular, cylindrical, spherical, and square.

5. The one-piece introducer of claim 1, wherein a hinge is located between the tube portion and the at least one finger tab portion.

6. The one-piece introducer of claim 5, wherein the finger tab portion, the hinge portion, and the tube portion form a seamless introducer.

7. A one-piece introducer comprising:
a tube;
a first finger tab, a second finger tab, and a valve formed at a proximal end of the tube as a single integral piece with the tube; and
a scoreline formed on the tube.

8. The one-piece introducer of claim 7, comprising a polymer, the polymer is selected from the group consisting of liquid crystal polymer, polyetheramide, polycarbonate, polyester with glass fiber, polyester with carbon filler, polyamide with glass fiber, thermoplastic elastomers, polyolefins and polyamide with carbon filler.

9. The one-piece introducer of claim 7, wherein the scoreline extends to a beveled distal tip of the tube portion.

10. The one-piece introducer of claim 7, wherein the tube is substantially hollow.

11. The one-piece introducer of claim 7, wherein the first finger tab and the second finger tab each have a shape which is one of substantially rectangular, cylindrical, spherical, and square.

* * * * *